United States Patent
Graham

(10) Patent No.: US 11,471,357 B2
(45) Date of Patent: *Oct. 18, 2022

(54) PNEUMATIC JOINT SEPARATOR FOR LOWER BODY ALIGNMENT

(71) Applicant: Richard A. Graham, Huntington Beach, CA (US)

(72) Inventor: Richard A. Graham, Huntington Beach, CA (US)

(*) Notice: Subject to any disclaimer, the term of this patent is extended or adjusted under 35 U.S.C. 154(b) by 574 days.

This patent is subject to a terminal disclaimer.

(21) Appl. No.: 16/410,832

(22) Filed: May 13, 2019

(65) Prior Publication Data
US 2019/0365589 A1    Dec. 5, 2019

Related U.S. Application Data

(63) Continuation of application No. 14/968,668, filed on Dec. 14, 2015, now Pat. No. 10,285,891, which is a continuation-in-part of application No. 12/970,539, filed on Dec. 16, 2010, now Pat. No. 9,241,820.

(51) Int. Cl.
*A61H 1/00* (2006.01)
*A63B 21/00* (2006.01)
(Continued)

(52) U.S. Cl.
CPC .............. *A61H 1/006* (2013.01); *A61F 5/01* (2013.01); *A63B 21/0004* (2013.01);
(Continued)

(58) Field of Classification Search
CPC ...... A61F 5/00; A61F 5/01; A61F 5/02; A61F 5/022; A61F 5/024; A61F 5/026;
(Continued)

(56) References Cited

U.S. PATENT DOCUMENTS 2,806,471 A   9/1957  Breese
3,068,002 A   12/1962  Balne
(Continued)

FOREIGN PATENT DOCUMENTS

DE    2638077       3/1977
JP    04327849 A   11/1992
(Continued)

OTHER PUBLICATIONS

Alf Breig, M.D., Adverse Mechanical Tension in the Central Nervous System, Copyright 1978, p. 17, figure A and B [4A].
(Continued)

*Primary Examiner* — Michael J Tsai
(74) *Attorney, Agent, or Firm* — Knobbe Martens Olson & Bear, LLP

(57) ABSTRACT

A leg muscle, abdominal muscle, and spinal exercise device adapted for imparting curvature to a lumbar or sacral spine of a user and for manipulating the spine and intervertebral discs with decompression force includes a frame for placement on a floor. The frame has a top surface and a bottom surface, wherein the top surface and bottom surface are in a spaced apart relationship forming a hollow portion there between. At least one inflatable bladder is carried by the top surface of the frame. A body strap attachment passes through the frame in non-fixed relationship and is partially disposed within the hollow portion for encompassing the user's thoracic-sacral spinal region and securing said frame. An elongate stirrup strap member is attachable to the body strap attachment thereby connecting to the user's spinal region. A stirrup is attachable to the stirrup strap member distal end.

20 Claims, 7 Drawing Sheets

(51) Int. Cl.
  *A61F 5/01* (2006.01)
  *A63B 23/02* (2006.01)
  *A63B 23/04* (2006.01)
  *A63B 21/04* (2006.01)

(52) U.S. Cl.
  CPC .... *A63B 21/00043* (2013.01); *A63B 21/0428* (2013.01); *A63B 21/15* (2013.01); *A63B 21/151* (2013.01); *A63B 21/4009* (2015.10); *A63B 21/4025* (2015.10); *A63B 21/4034* (2015.10); *A63B 23/0205* (2013.01); *A63B 23/0216* (2013.01); *A63B 23/0233* (2013.01); *A63B 23/0238* (2013.01); *A63B 23/0494* (2013.01); *A63B 2213/00* (2013.01); *A63B 2225/01* (2013.01); *A63B 2225/62* (2013.01)

(58) Field of Classification Search
  CPC ......... A61F 5/028; A47G 9/00; A47G 9/1009; A47G 9/1027; A61H 1/00; A61H 1/02; A61H 1/0218; A61H 1/0222; A61H 1/0229; A61H 1/0292; A61H 2205/081; A61H 2201/1623
  See application file for complete search history.

(56) References Cited

U.S. PATENT DOCUMENTS

| | | |
|---|---|---|
| 3,521,623 A | 7/1970 | Nichols |
| 3,667,457 A | 6/1972 | Zumaglini |
| 3,765,412 A | 10/1973 | Ommaya |
| 3,899,797 A | 8/1975 | Gunst |
| 3,974,827 A | 8/1976 | Bodeen |
| 4,024,861 A | 5/1977 | Vincent |
| 4,043,668 A | 8/1977 | Goetz |
| D247,312 S | 2/1978 | Zeiss |
| 4,114,611 A | 9/1978 | Lyle |
| 4,135,503 A | 1/1979 | Romano |
| 4,159,020 A | 6/1979 | von Soiron |
| 4,161,946 A | 7/1979 | Zuesse |
| 4,194,501 A | 3/1980 | Watt |
| 4,391,466 A | 7/1983 | Smith |
| 4,456,249 A * | 6/1984 | Calabrese ............ A63B 21/154 482/124 |
| 4,463,947 A | 8/1984 | Kloenne |
| 4,583,255 A | 4/1986 | Mogaki |
| 4,583,532 A | 4/1986 | Jones |
| 4,669,455 A | 6/1987 | Bellati |
| 4,736,736 A | 4/1988 | Moers |
| RE32,791 E | 11/1988 | Saunders |
| 4,805,603 A | 2/1989 | Cumberland |
| 4,838,613 A | 6/1989 | Smith |
| D302,592 S | 8/1989 | Holmes |
| 4,981,131 A | 1/1991 | Hazard |
| 4,995,378 A | 2/1991 | Dyer |
| 5,003,968 A | 4/1991 | Mars |
| 5,062,414 A | 11/1991 | Grim |
| 5,067,483 A | 11/1991 | Freed |
| 5,070,865 A | 12/1991 | Iams |
| 5,147,287 A | 9/1992 | Jewell |
| 5,154,186 A | 10/1992 | Laurin |
| 5,181,904 A | 1/1993 | Cook |
| 5,190,348 A | 3/1993 | Colasanti |
| 5,201,761 A | 4/1993 | Serola |
| 5,207,627 A * | 5/1993 | Doran ................. A61H 1/0218 482/114 |
| 5,207,716 A | 5/1993 | McReynolds |
| 5,211,162 A | 5/1993 | Gillen, Jr. |
| 5,232,424 A | 8/1993 | Pearson |
| 5,244,393 A | 9/1993 | Perry |
| 5,258,017 A | 11/1993 | Myers |
| 5,279,310 A | 1/1994 | Hsien |
| 5,292,175 A | 3/1994 | Artz |
| 5,305,750 A | 4/1994 | Makita |
| 5,338,276 A | 8/1994 | Jull |
| 5,382,226 A | 1/1995 | Graham |
| 5,403,266 A | 4/1995 | Bragg |
| 5,407,418 A | 4/1995 | Szpur |
| 5,410,472 A | 4/1995 | Anderson |
| 5,423,861 A | 6/1995 | Kelley |
| 5,472,401 A | 12/1995 | Rouillard |
| 5,538,486 A | 7/1996 | France |
| 5,560,056 A | 10/1996 | Tai |
| 5,562,324 A | 10/1996 | Massara |
| 5,569,176 A | 10/1996 | Graham |
| 5,588,941 A * | 12/1996 | Scott .................... A61H 1/0218 482/131 |
| 5,713,841 A | 2/1998 | Graham |
| 5,738,640 A | 4/1998 | Carlson-Orsi |
| 5,772,281 A | 6/1998 | Massara |
| 5,906,586 A | 5/1999 | Graham |
| 5,933,890 A | 8/1999 | Codd |
| 6,007,501 A | 12/1999 | Cabados |
| 6,007,507 A | 12/1999 | Ledany |
| 6,039,737 A | 3/2000 | Dyer |
| D445,505 S | 7/2001 | Shapiro |
| 6,305,040 B1 | 10/2001 | Myler |
| 6,390,997 B1 | 5/2002 | Vitko |
| 6,506,174 B1 | 1/2003 | Saunders et al. |
| 6,544,152 B2 * | 4/2003 | Rosati ................. A63B 21/055 482/126 |
| 6,592,184 B1 | 7/2003 | Segal et al. |
| 6,648,844 B2 | 11/2003 | Kamerman |
| D486,235 S | 2/2004 | Haddock |
| 6,899,690 B2 | 5/2005 | Saunders et al. |
| D508,566 S | 8/2005 | Graham |
| 7,022,094 B2 | 4/2006 | Buckman et al. |
| 7,059,678 B1 | 6/2006 | Taylor |
| 7,060,085 B2 | 6/2006 | Graham |
| 7,066,897 B2 | 6/2006 | Huang |
| 7,104,935 B2 | 9/2006 | Matsuoka |
| 7,108,671 B2 | 9/2006 | Saunders et al. |
| 7,264,601 B2 | 9/2007 | Liao |
| 7,566,314 B2 | 7/2009 | Saunders et al. |
| 7,634,949 B2 | 12/2009 | Lodge |
| 7,967,735 B2 | 6/2011 | Hudswell |
| 8,029,453 B2 | 10/2011 | Graham |
| 8,083,705 B2 | 12/2011 | Saunders et al. |
| 8,100,846 B1 | 1/2012 | LaMonica |
| 8,323,223 B1 | 12/2012 | Woggon et al. |
| 8,734,372 B1 | 5/2014 | Graham |
| 8,764,693 B1 | 7/2014 | Graham |
| 9,241,820 B2 | 1/2016 | Graham |
| 9,801,779 B2 | 10/2017 | Breibart et al. |
| 10,406,397 B1 | 9/2019 | Graham |
| 2003/0088200 A1 | 5/2003 | Saunders et al. |
| 2003/0125650 A1 | 7/2003 | Grosso |
| 2003/0130696 A1 | 7/2003 | Hurd |
| 2004/0143206 A1 | 7/2004 | Saunders et al. |
| 2006/0161087 A1 | 7/2006 | Carter et al. |
| 2006/0206046 A1 | 9/2006 | Saunders |
| 2007/0079415 A1 | 4/2007 | Carlson |
| 2007/0105696 A1 | 5/2007 | Castel |
| 2007/0293796 A1 | 12/2007 | Graham |
| 2008/0248936 A1 | 10/2008 | Ferriss et al. |
| 2009/0118657 A1 | 5/2009 | Saunders et al. |
| 2009/0187127 A1 | 7/2009 | Buckman et al. |
| 2017/0100638 A1 | 4/2017 | Breibart |

FOREIGN PATENT DOCUMENTS

| | | |
|---|---|---|
| WO | WO 1987/000424 | 1/1987 |
| WO | WO 1996/014810 A2 | 5/1996 |
| WO | WO 1996/014810 A3 | 8/1996 |

OTHER PUBLICATIONS

Cailliet, R., M.D., Low Back Pain Syndrome, Edition 4, Pain Series, Copyright 1994, [1 A] p. 5, [1B] pp. 6-8, [1C] pp. 6-8.

Harrison, Donald D., Ph.D., M.S., D.C., The Physics of Spinal Correction, Copyright 1994, [2A] Fig. 3-3. [2B] Fig 1-21. [2C] Fig 3-3 and Fig 7-6, [2D] Fig 3-6., [2E] Figures 7-2, 7-3.

(56) References Cited

OTHER PUBLICATIONS

Kirkaldy-Willis, M.A., M.D., F.R.C.S., (Edin)(C), F.A.C.S., Managing Low Back Pain, Second Edition, Copyright 1988, [3A] p. 306.
Shealy, Norman, M.D., Ph.D., 2008 IRB Approved MRI Study of the Effects of Axial Linear Traction and Expanding Ellipsoidal Decompression (EED®) via Posture Pump® on Cervical Curve, Disc Protrusions and Disc Height, Copyright 2008, Practical Pain Management, Mar. 2010.
Shealy, Norman, M.D., Ph.D., 2006 IRB Approved Study of Cervical Decompression Treatment, Copyright 20008, Practical Pain Management, Apr. 2007.

\* cited by examiner

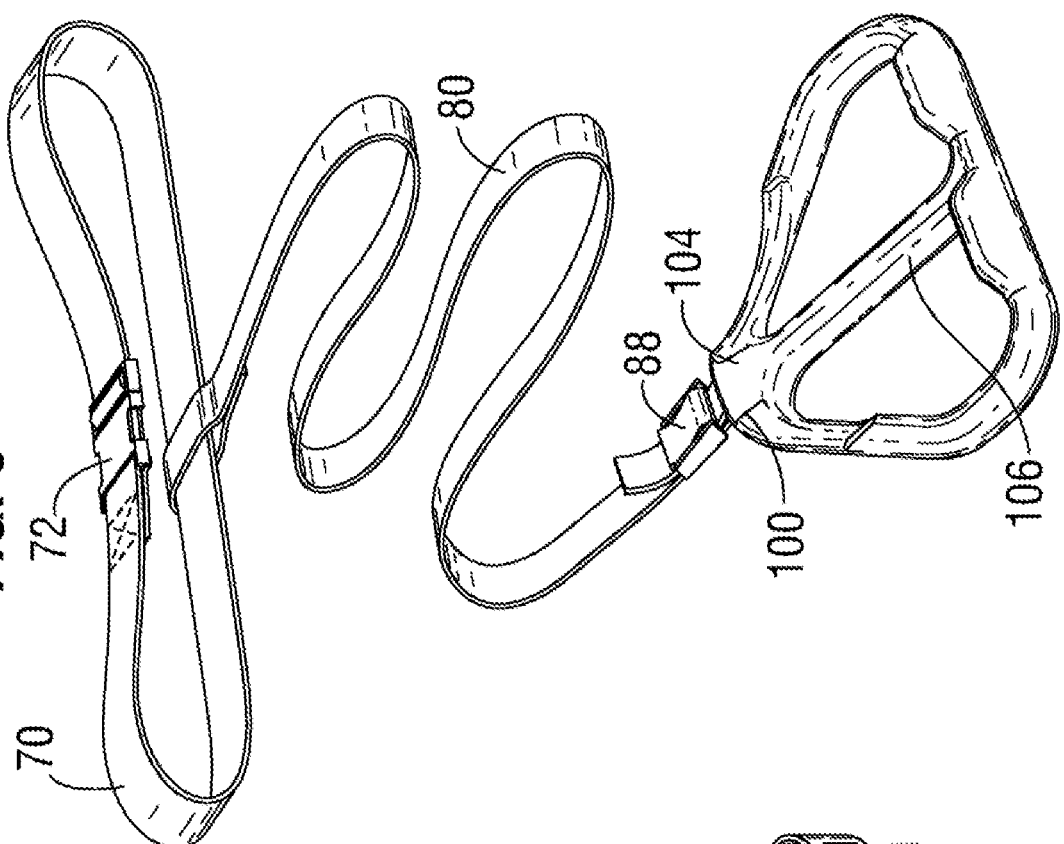
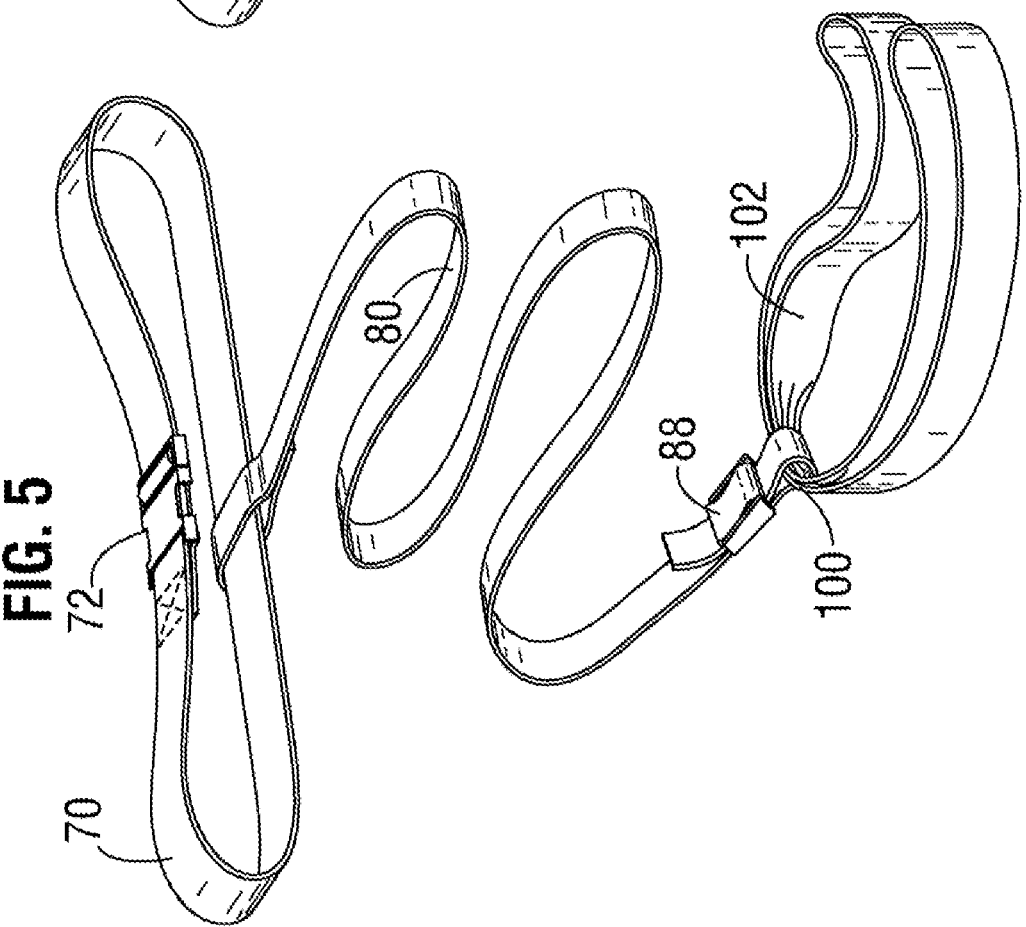

PNEUMATIC JOINT SEPARATOR FOR LOWER BODY ALIGNMENT

CROSS-REFERENCE TO RELATED APPLICATIONS

This application is a continuation-in-part application to application Ser. No. 12/970,539 filed on Dec. 16, 2010 the entire contents of which are fully incorporated herein with this reference.

DESCRIPTION

Field of the Invention

The present invention relates to an exercising device directed at alignment of the lower body and spinal vertebrae. More specifically, the present invention relates to the apparatus and methods for decompressing the spinal vertebrae using the pulling forces of the lower body, leg muscles, and abdominal muscles to urge and correct aberrant spinal vertebrae postures.

Background of the Invention

The spinal column is a bony column forming the main structural support of the skeleton of a human being and it consists of bony vertebrae linked by flexible joints and held together by ligaments and flexible gelatinous discs of cartilage. The spinal column of an adult human being consists of thirty-three vertebrae in which the last nine of these are fused to form the sacrum and the coccyx at the back of the pelvis. The 24 movable vertebrae are the 7 cervical (neck), 12 dorsal, and 5 lumbar. The vertebrae form a column for the skeleton and the arches are positioned so the space enclosed is an effective tube or canal. This houses and protects the spinal cord and within it the spinal fluid circulates. Without the seepage of fluids into the spinal column, the discs will further dehydrate, which may result in further loss of mobility, crippling, and even nerve damage. Thus, nutrient transport of fluids surround the spinal column is important in maintaining spinal health. It is known that the spine has a number of curvatures along the sagittal plane, namely, the cervical and lumbar curvatures in which the spine is convex toward the front of the body and the dorsal and sacral curvatures in which the spine is convex toward the back of the body. These alternating curves provide strength and balance to the body and are essential to allowing a person to walk upright. The lumbar and cervical curves of the spine normally define forward curves of about 35 to about 45 degrees whereby weight is distributed relatively evenly on individual vertebral surfaces and discs.

In individuals with lost or reversed cervical and lumbar spinal curves due to injury, illness, genetic predisposition, habitual microtrauma or simply poor posture, the weight of the body bears forwardly on the soft, non-bony intervertebral discs, inhibiting fluid transfer and causing the discs to wear, dehydrate and degenerate. Over time, these individuals exhibit a significant loss of natural joint movement. Lack of natural movement in the spine over time causes a reduction in the imbibition of nutrient rich fluids that normally lubricate and maintain flexibility of the spine. Without this seepage of fluids into the spinal column, the discs will further dehydrate, which may result in further loss of mobility, crippling and possible nerve damage. It is further noted that the intervertebral discs' indigenous vascular fluid supply disappears at approximately 20 years of age. Thus, active nutrient transport of fluids surrounding the spinal column is particularly important to maintaining spinal health of adults.

In addition to spinal traction devices which are well known for stretching the spine longitudinally in order to restore lost mobility, devices have been developed for either passively or actively restoring the normal curves of the spine to prevent the disabling effects of lost or impaired curvature mentioned hereinabove. An example for at home use device includes a Method and Portable Apparatus for Spinal Adjustment disclosed in U.S. Pat. Pub. No. US2003/0130696 to Hurd. In this device, a user employs the effects of gravity combined with simple leverage over a convex rigid surface to adjust the user's spine. Another example of a passive device includes, for example, the Spinal Column Correction Device disclosed in U.S. Pat. No. 5,279,310 to Hsein. In this device, a user is strapped to a series of raised supports that define what the normal curvatures of the spine should be. According to the inventor, the weight of the user's body will bear against the raised supports to correct abnormal curvature in the spine.

An example of a useful device that actively exercises the abdominal muscle and spine is disclosed in U.S. Pat. No. 7,060,085 to Graham entitled Rocking Vectored Pneumatic Joint Separator Inflatable Cervical Traction and Exercising Device, this patent being incorporated by this specific reference herein. An abdominal muscle and spine-exercising device in accordance with the invention generally includes a frame having a top surface and a bottom surface. A first arched projection is disposed in the top surface along with a first inflatable bladder disposed on the first arched projection for directly bearing against lower thoracic and upper lumbar vertebrae of a user's spine in a first direction. A second inflatable bladder is disposed on the first arched projection for directly bearing against the mid-lumbar and lumbo-sacral vertebrae of the spine in a second direction. The first and second directions are divergent along a sagittal plane of the user in order to enhance an elliptical curve in the thoraco-lumbar/lumbo-sacral spine. A second arched projection is disposed on the bottom surface for enabling the frame and bladders to be rocked by the user in a direction transverse to a longitudinal axis of the frame. This rocking action provides exercise for the abdominal, low-back and pelvic muscles while the spine is inflated into an elliptical shape.

Another useful device that actively exercises the normal lordotic, i.e. forward, curves of a spine is disclosed in U.S. Pat. No. 5,382,226 to Graham entitled Inflatable Cervical Traction and Exercising Device, this patent being incorporated herein by this specific reference. In the Graham patent, a device is disclosed which utilizes an inflatable bladder for actively forcing the cervical spine into a forward semi-circular curve. This exercising of the spine promotes fluid imbibition through the spinal vertebrae and intervertebral discs.

U.S. Pat. No. 5,906,586 to Graham provides for a device and method for maintaining spinal health which utilizes a dual action air chamber defining multiple vectors of force to be applied to a spine, particularly to the lumbar spinal region this patent being incorporated herein by this specific reference. The device gradually lifts and separates the vertebrae in a manner that surpasses the effectiveness and comfort of conventional traction devices and passive spinal correction devices using a frame for aligning the upper spine.

U.S. Pat. Application 2007/0293796 is incorporated herewith by reference, to Graham provides a leg carrier slidably disposed in a conventional manner on a table for providing pelvis translation. In order to prevent or control twisting of the lower body, knee fenders may be fixed to the leg carrier. A lumbar sacral unit disposed on the support table between the cervical device and carrier is provided for enhancing an elliptical arch in the users' lower spine. The lumbar sacral unit is also described in U.S. Pat. Nos. 5,713,841, 5,569,176, and D508,565 by Dr. Graham and are incorporated herewith by specific reference in their entirety.

The present invention provides for a combination leg muscle, abdominal muscle and spine-exercising device utilizing the vectoring of the earlier Graham work and further providing for apparatus capable of exercising, decompressing, and aligning the lower body and leg muscles while the spinal vertebrae are pneumatically molded into the accepted elliptical configuration of the thoraco-lumbar/lumbo-sacral spine to the legs.

SUMMARY OF THE INVENTION

Accordingly, in accordance with the present invention, a leg muscle, abdominal muscle, and spinal exercise device generally is provided for redefining curvature to the lumbar/sacral spine and for manipulating the spine and intervertebral discs with decompression force from the lower body. This device generally comprises a means for manipulating and redefining the curvature of the spine and a frame.

Specifically, the means for manipulating and redefining the curvature of the spine includes a top surface along with a first inflatable bladder disposed for directly bearing against lower thoracic and upper lumbar vertebrae of a user's spine in a first direction. A second inflatable bladder is disposed for directly bearing against the mid-lumbar and lumbo-sacral vertebrae of the spine in a second direction to enhance the lower body strength and curve in spine. The adjacent inflated bladders, or alternately inflated bladders, provide diverging forces against the user's spine and thereby cause stretching and longitudinal aligning of the spinal vertebrae while promoting fluid imbibition throughout the vertebrae and discs. Thus, initially, the inflated first bladder may lift the thoracic-lumbar spinal vertebrae while the inflated second bladder may lift the lumbar-sacral spinal vertebrae thereby manipulating and redefining the semi-elliptical curvature in the spine.

More specifically, a body strap attachment for encompassing the user's body and securing the frame connects to an elongate stirrup strap member having a proximal end and a distal end. Preferably, the body attachment connects two ends of a strap, for example by means of a buckle, for adjustably securing the frame against the user's lumbar region.

The elongate stirrup strap member having a proximal end attached to the body strap attachment thereby connecting to the user's spine and frame, and a distal end attached to a stirrup for encompassing the user's feet/legs to enable decompression force from the lower body to the spine. Alternatively, the elongate stirrup strap member may include an attachable pressure gauge for measuring the decompression force exerted by the feet/legs on the lower body. A handheld monitor communicates with the pressure gauge for the user to monitor applied decompression or exercise force.

Even more specifically a stirrup attachment engagable by the user's feet/legs is provided for enabling pulling force from the legs and lower body to the spine. This stirrup attachment further enables the user to exercise the leg muscles while decompressing the thoraco-lumbar/lumbo-sacral spinal vertebrae which are pneumatically molded by the inflated bladders into the accepted elliptical configuration. Thus the spinal vertebrae are urged and molded into the natural elliptical alignment, the joints are lubricated and aligned, and the lower body muscles including the legs, abdominal, lower-back, and pelvic muscles are stretched and exercised.

Alternatively, the exercise device adapted for the user to exercise and strengthen the lower body muscles the proximal end is attached to the body strap attachment without the frame spine for enabling decompression pulling force aligned from the legs and lower body to the spine.

The device described hereinabove is suitable for performing a method for decompressing the spine and for exercising the lower body muscles, leg muscles, abdominal muscles. comprising the steps of: (a) providing a frame attachable against the user's spine with first and second bladders disposed on a top of said frame and a rocker projection disposed on a bottom of said frame: (b) inflating a bladder bearing against the lower thoracic and upper lumbar vertebrae and inflating another bladder hearing against the middle lumbar and lumbar-sacral vertebrae in order to create traction and spinal arc in the lower spinal region and to stretch lower body muscle groups, leg muscles; (c) inflating and exhausting alternatively the bladder bearing against the lower thoracic and upper lumbar with the bladder bearing against the middle lumbar and lumbo-sacral vertebrae; (d) encompassing the user's waist/lumbar region and securing the frame with a hotly strap attachment; (e) connecting the body strap attachment to an elongate stirrup strap attached to tension gauge for monitoring decompression three and attached to a stirrup for encompassing the user's feet/legs; (f) engaging slidably the user's feet/legs into the stirrup for enabling stress aligned from the legs and lower body to the spine; (g) creating aligned decompression forces between the leg muscles and lower abdominal muscles by pulliing the stirruped legs/feet in a direction away from the spine away from the spine to decompress, ergo, and align the spinal vertebrae; (h) monitoring the tension gauge with a handheld monitor and controlling the decompression forces between the leg muscles and lower abdominal. muscles and repeating the exercising force to strengthen the lower body, spine, and legs.

Alternatively, the device described hereinabove is suitable for performing a method, in accordance with the present invention, for exercising the lower body, legs, and spine to enable and promote lower body and spinal alignment, comprising the steps of: (a) encompassing the user's thoracic-sacral spinal vertebrae region and securing the frame with a body strap attachment (b) connecting the body strap attachment to an elongate stirrup strap attached to tension gauge for monitoring decompression force and attached to a stirrup for encompassing the user's feet/legs; (c) engaging slidably the user's feet/legs into the stirrup for enabling stress aligned from the legs and lower body to the spine; (d) creating aligned decompression forces between the leg muscles and lower abdominal muscles by pulling the stirruped legs/feet in a direction away from the spine away from the spine to decompress, urge, and align the spinal vertebrae; (e) monitoring the tension gauge with a handheld monitor and controlling the decompression forces between the feet/leg muscles and lower abdominal muscles and repeating the exercising force to strengthen the lower body, spine, and legs.

BRIEF DESCRIPTION OF THE DRAWINGS

The accompanying drawings illustrate the invention. In such drawings:

FIGS. 5-6 illustrate perspective top views of the body strap attachment which encompasses the user's spinal region, an elongate stirrup strap, and a stirrup. FIG. 5 illustrates the stirrup as an attachable looped band while FIG. 6 illustrates the stirrup as a partitioned annulus (ring) for aligning and supporting the feet and the lower body;

FIG. 7 illustrates the user in a relaxed position and FIG. 8 illustrates the user in the extended lower body position applying decompression force to the spine and inflated bladders against the user's spine to expand and redefine the curvature in the spine;

DETAILED DESCRIPTION OF THE PREFERRED EMBODIMENTS

Figure 1:
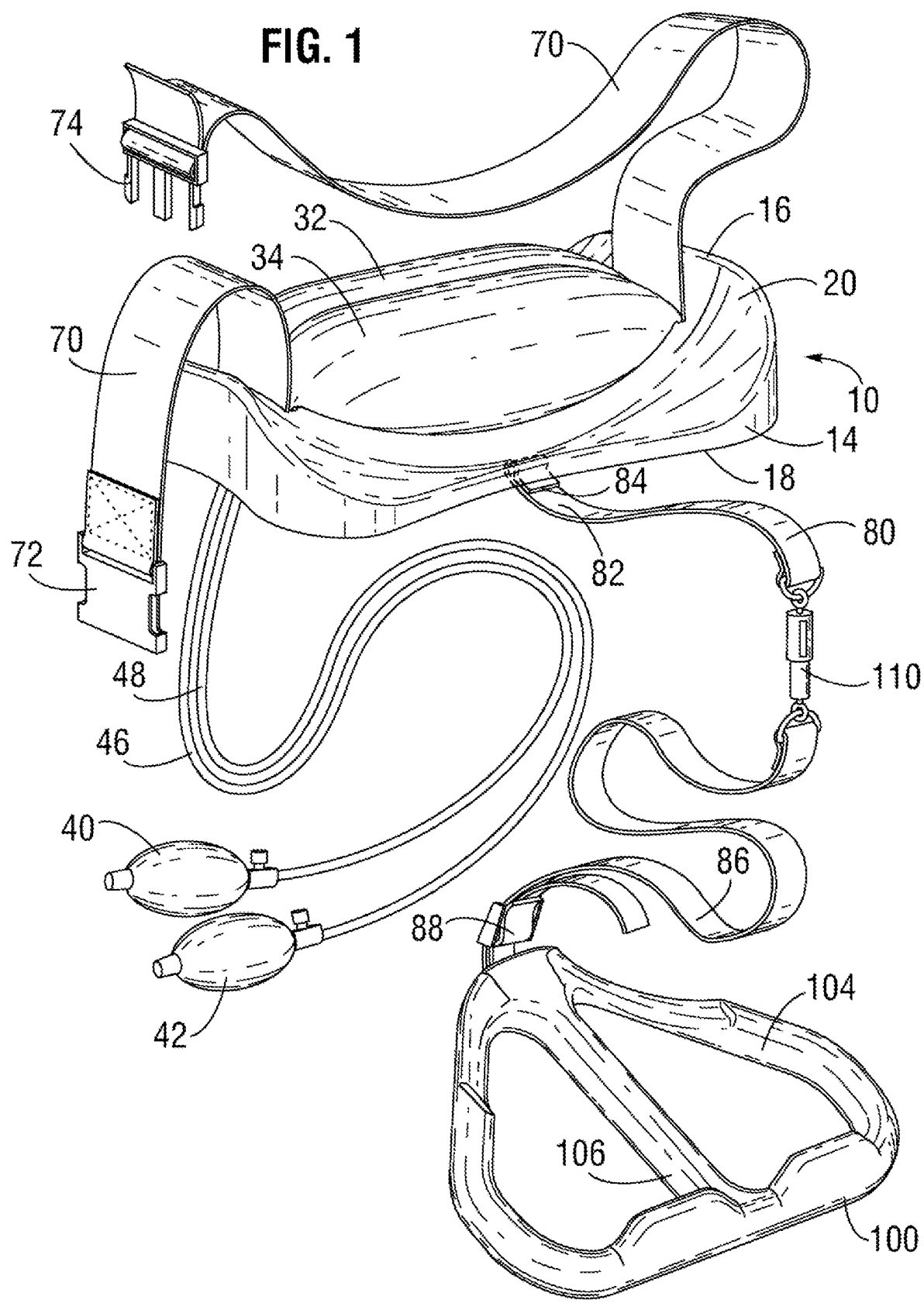
FIG. 1 is a perspective view of the lower body and spinal exercise device in accordance with the present invention, including a frame having two inflatable bladders disposed thereon, a pair of handheld pumps for bladder inflation, a body attachment attached to a stirrup strap, a tension gauge, and an attached stirrup for feet/legs.
Figure 2:
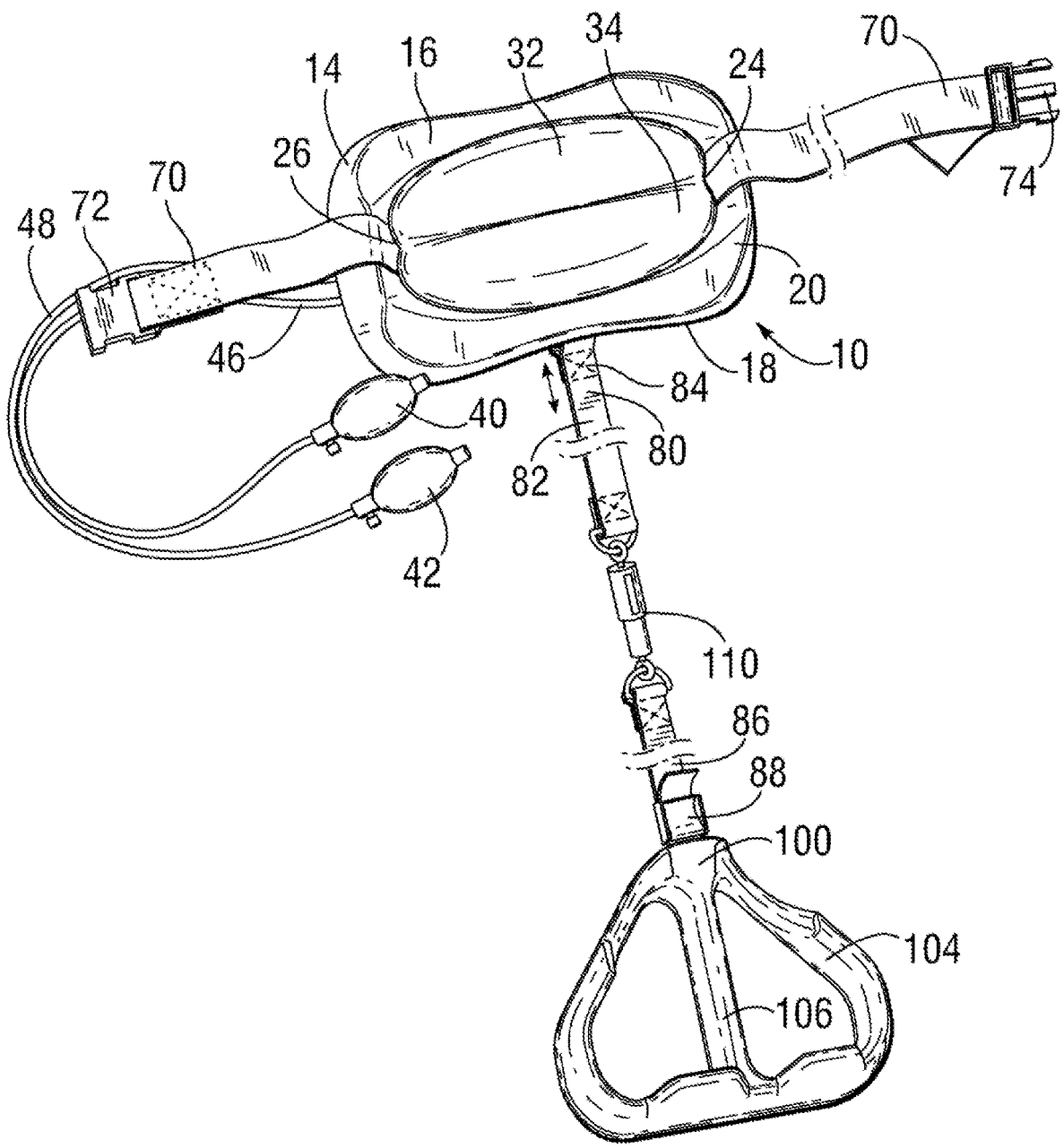
FIG. 2 illustrates a perspective view of the top side of the lower body and spinal exercise device positioned for use in accordance with FIG. 1.
Figure 3:
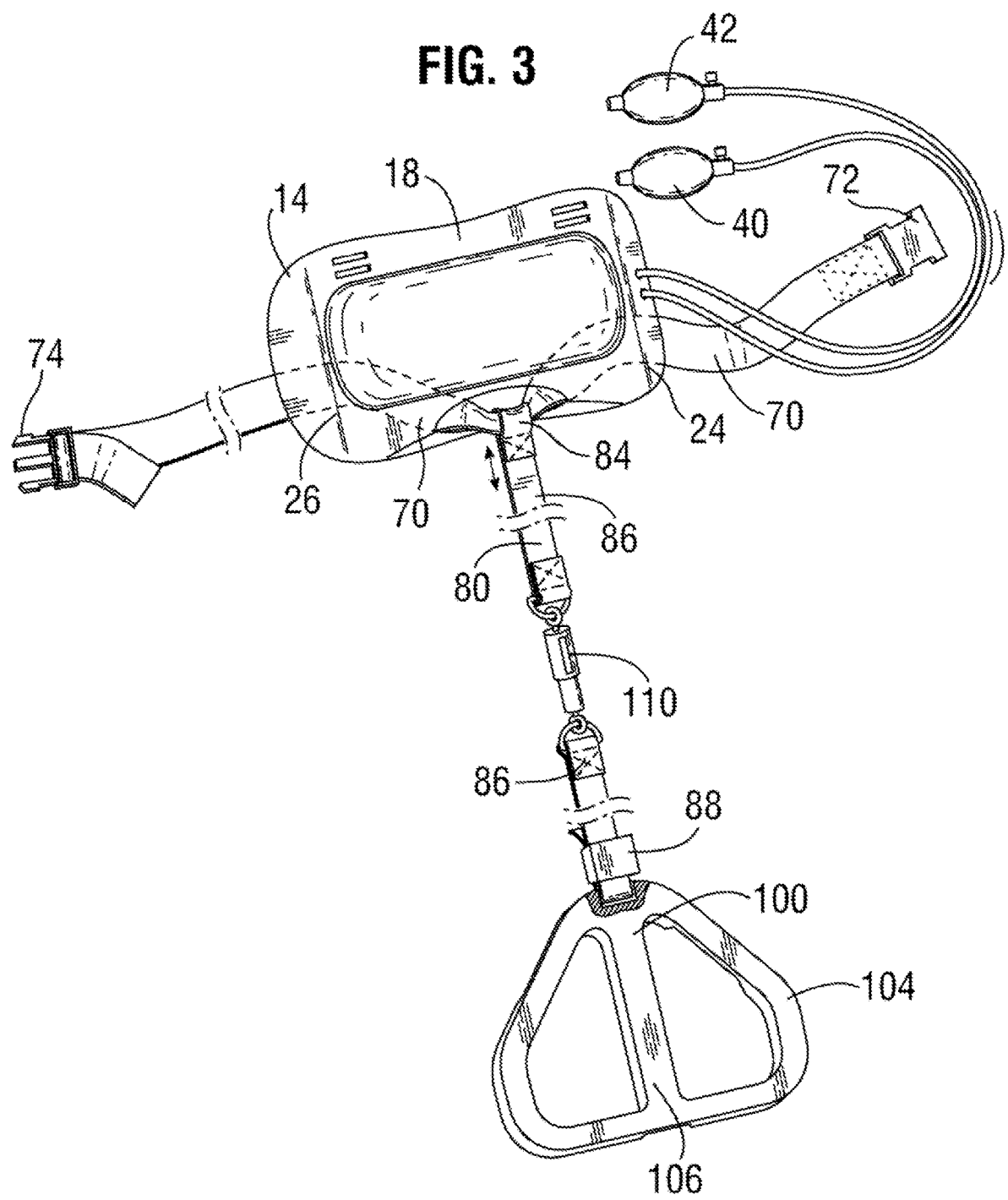
FIG. 3 illustrates a view of the bottom side of the lower body and spinal exercise device positioned for use in accordance with FIG. 1.
Figure 4:
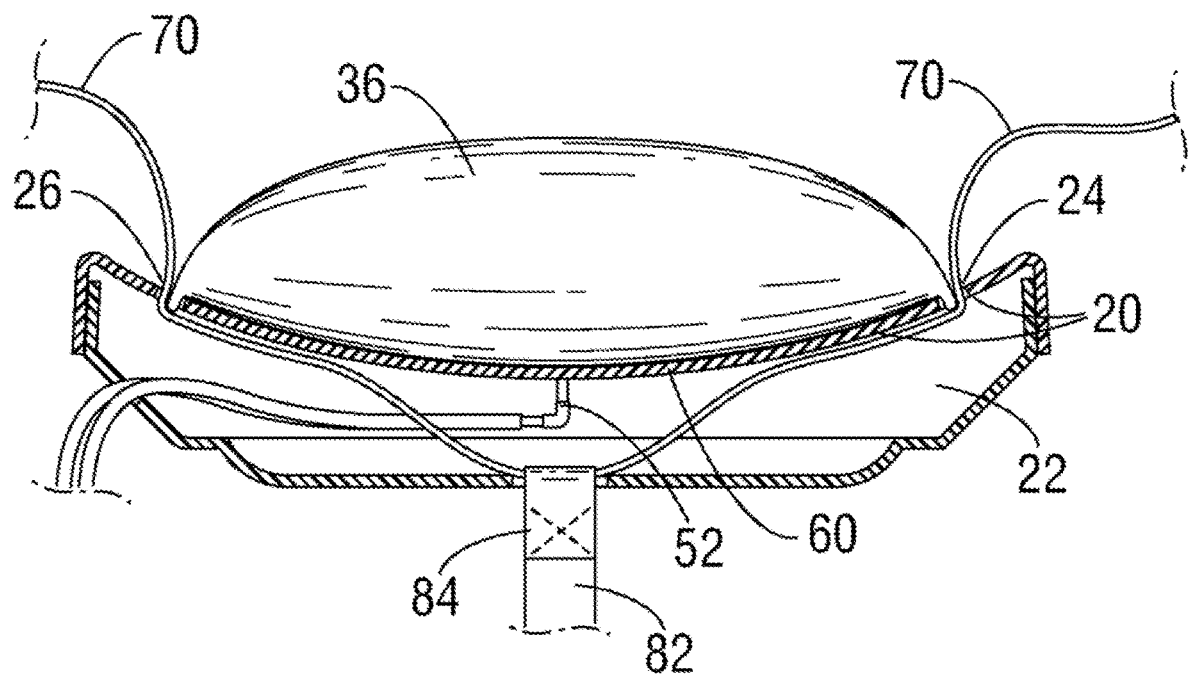
FIG. 4 is a cross sectional view of the device in accordance with the invention showing the inflatable bladder disposed on a frame, connected to flexible pump tubing, hollow and slot portions of the frame, and a body strap attachment interconnected to the frame slots and to the elongate stirrup strap.

With reference to FIGS. 1-4 there is shown a leg muscle, abdominal muscle, and spinal exercise device 10 which includes a frame 14 having a top surface 16 and a bottom surface 18. As best seen in FIGS. 1 and 4, the top surface 16 includes a concave surface 20 and, as best seen in FIG. 3 a bottom surface 18.

The frame 14 structure is preferably molded in suitable lightweight plastic for enabling interconnection of the two inflatable bladders 32, 34 to the top surface 16. As best seen in FIG. 4, the concave surface 20 of the frame 14 includes a hollow portion 22 and slotted 24, 26 portions for enabling interconnection the air bladders 32, 34 and interconnection of the body strap attachment 70.

With reference to FIG. 2, the inflatable bladders 32, 34 carried by the frame 14 are defined by an upper 32 and a lower portion 34 which are disposed proximate a center of the frame top surface 16. With reference to FIGS. 2 and 4, the air bladders 32, 34 are pneumatically inflated and deflated through the use of hand held pumps 40, 42 or bulbs, respectively through flexible tubing 46, 48 lines and fittings 52, 54 coupled to the bladders 32, 34 on the frame top surface underside 60.

Figure 7:
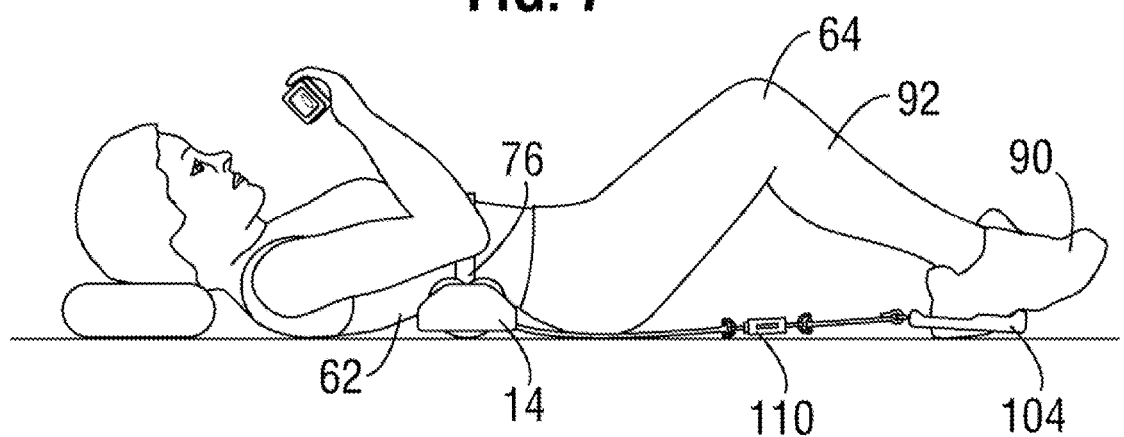
FIGS. 7-8 illustrate the use of the lower elongate stirrup strap member including an optionally attachable tension gauge for measuring the decompression force and a handheld monitor for communication with the tension gauge.
Figure 8:
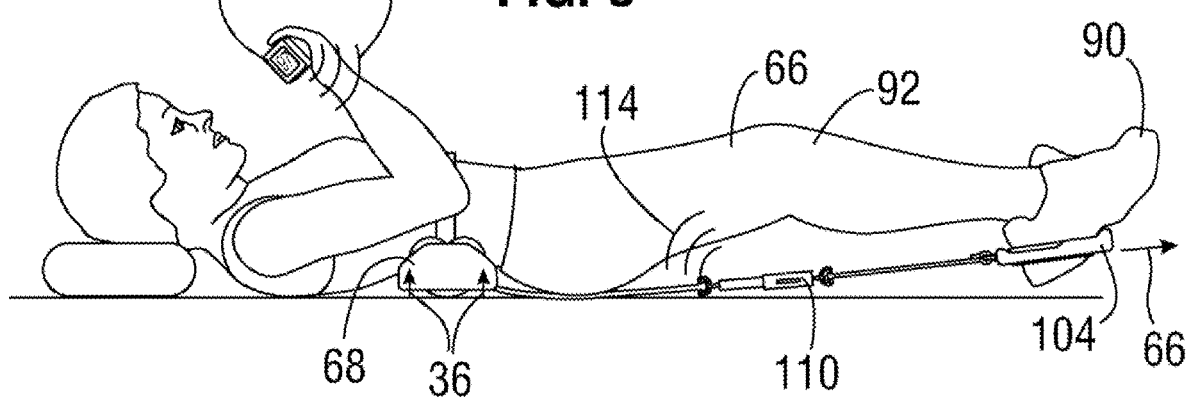

As illustrated in FIGS. 7 and 8, the inflatable bladders 32, 34 disposed on the frame concave top surface 16 bear directly against the user's spine while frame 14 supports the user's body contour 62. FIG. 7 shows the user at rest in an aligned position for exercise. FIG. 8 shows the user applying longitudinal alignment force 66 and enhanced spinal arc 68 created upon inflation 36 of the upper bladder 32 bearing against the lower thoracic and upper lumbar vertebrae and upon inflation of a lower bladder 34 bearing against the middle lumbar and lumbo-sacral vertebrae. The arrangement of the frame 14 and bladders 32, 34 is described in U.S. Pat. Nos. 5,906,586 and 7,060,085 to Graham which are to be incorporated herewith in their entirety for describing suitable bladders for use with the present invention and their position.

As seen in FIGS. 1-4, a body strap attachment 70 may be fitted through corresponding slots 24, 26 in the top surface 16 of the frame and fastened in a suitable manner. Two ends of the body strap attachment 70, shown in FIGS. 1-3, may include a buckle 72 on one end and a buckle fitting 74 on the other end for adjustably securing the body strap 70 and the frame 14 to the contour of the user's waist/lumbar spinal region 62, In an alternative embodiment depicted in FIGS. 5 and 6, the user may detach the frame 14 and use the body strap attachment 70 without the frame 14 or inflatable bladders 32, 34.

With reference to FIGS. 1, 5 and 6, there is shown an elongate stirrup strap member 80 having a proximal end 82 and a distal end 86. Both ends of the elongate stirrup strap member 80 include at least one loop for fastening the proximal end 84 to the body strap attachment 70 and another loop for fastening the adjustable distal end 88 to the stirrup 78. As best seen in FIG. 3 the elongate stirrup strap member 80 include at least one loop for fastening the proximal end 84 to the body strap attachment and is engaged with the bottom surface of the frame 18. FIG. 5 illustrates a stirrup 100 as a slidably looped band 102 attached to the loop stirrup strap distal end 88. FIG. 6 illustrates the stirrup 100 as annulus 104 attached to the adjustable stirrup strap distal end 88. As best seen in FIG. 8, the annulus 104 stirrup is shown with a partition 106 and a support for each foot 90 which aligns each leg 92 with the pelvis and spine while applying decompression force 94 to the spine.

With specific reference to FIGS. 7-8, in an alternative embodiment, a removable tension gauge 110 is coupled to the stirrup strap 80. A handheld monitor 112 communicates 114 with the tension gauge 110 thereby enabling the user to simultaneously view the tension measurement on the handheld monitor 112 while applying decompression tension force 94 from the feet 90 and legs 92 to the spine. The tension gauge 110 and handheld monitor 112 enabling the user to simultaneously view the tension measurement may be of a conventional design. FIG. 7 illustrates the user in a relaxed longitudinal aligned 64 position and FIG. 8 illustrates the user in the extended lower body position applying decompression force 94 to the spine and applying longitudinal stretching force 66 with inflated bladders 32, 34 against the spine.

Figure 9:
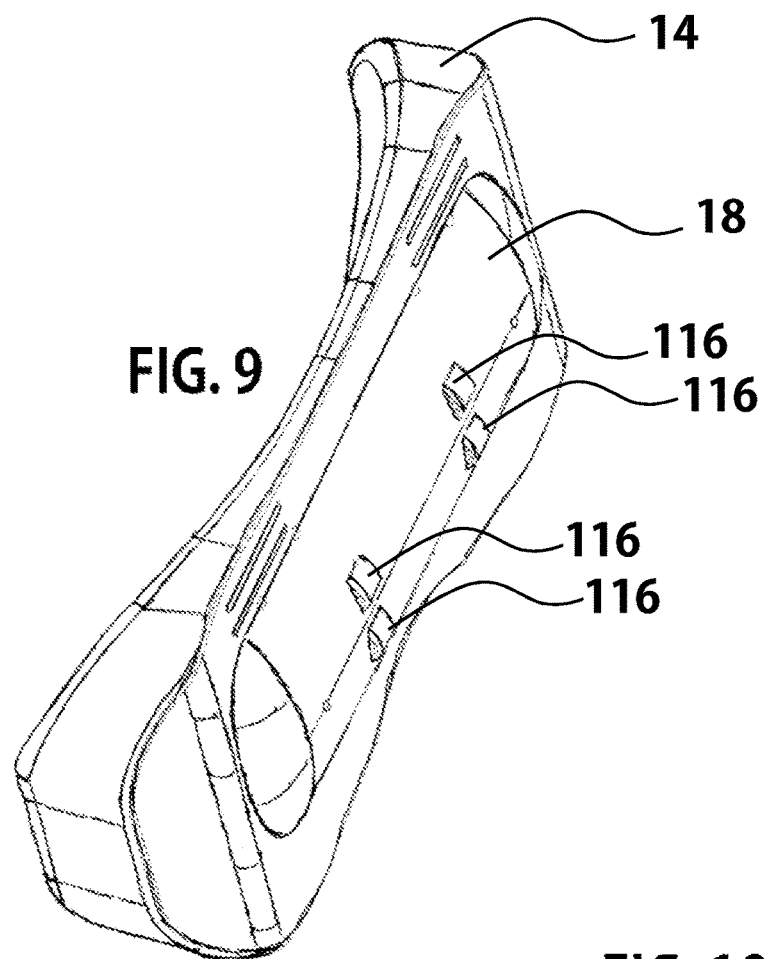
FIG. 9 is a perspective view of an exemplary frame with wheels.

With specific reference to FIG. 9 there is shown an embodiment of a frame 14 having plurality of wheels 116 rotatably attached along the bottom surface 18. The wheels 116 help to allow the frame 14 to move easily when it is used upon a hard surface, such as tile, concrete or wood. The wheels 116 are recessed into the frame 14 such that only a portion of the wheels 116 extend beyond the bottom surface 18. This helps to allow the frame 14 to still work properly on non-hard surfaces such as carpet. The plurality of wheels 116 can be at least one wheel, but is also understood to range from one wheel to many wheels.

Figure 10:
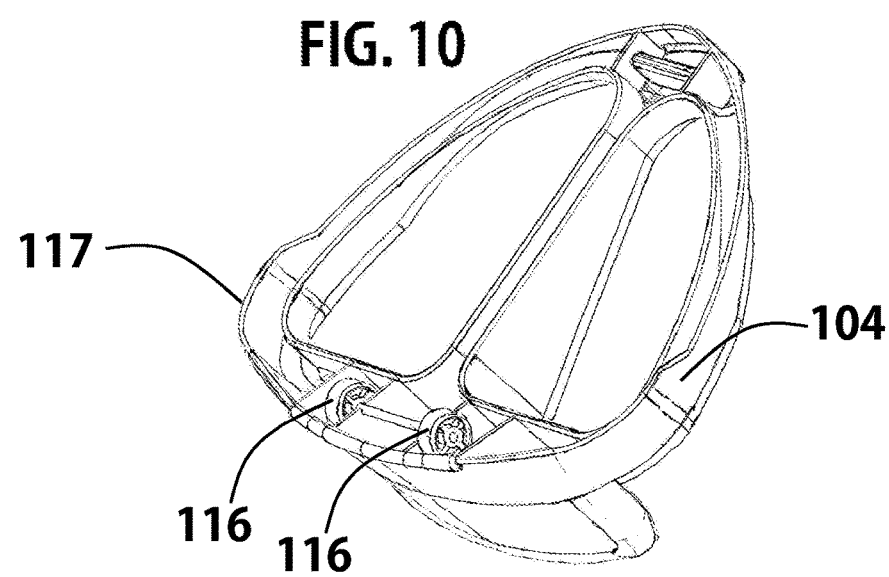
FIG. 10 is a perspective view of an exemplary stirrup with wheels.

With specific reference to FIG. 10 there is shown a stirrup 104 that now also includes a plurality of wheels 116. Just as with the frame 14 of FIG. 9, the wheels 116 of FIG. 10 allow the stirrup 104 to move easily when it is used upon a hard surface, such as tile, concrete or wood. Again, the wheels 116 can be recessed into the stirrup such that only a small portion of the wheels 116 extend beyond a bottom surface 117 of the stirrup 104. The plurality of wheels 116 can be at least one wheel, but is also understood to range from one wheel to many wheels.

The previous Abstract taught a spinal disc/joint, lower body, leg muscle, abdominal muscle and spine exercising device and method adapted for imparting curvature and manipulating the thoracic/lumbar/sacral spine and for decompressing/hydrating spinal discs and exercising the lower body are provided. The device may generally include a frame and apparatus for redefining the curvature of the spine and exercising the lower body muscles. Specifically, the apparatus for manipulating and imparting curvature of the spine includes a frame for placement on a floor and having a top surface, along with a first inflatable bladder disposed for directly bearing against lower thoracic and upper lumbar vertebrae of a user's spine in a first direction. A second inflatable bladder is disposed for directly bearing against the mid-lumbar and lumbo-sacral vertebrae of the spine in a second direction. The adjacent inflated bladders, or alternately inflated bladders, provide diverging forces against the user's spine and thereby cause stretching and longitudinal aligning of the spinal vertebrae while promoting fluid imbibition throughout the vertebrae and discs. Thus the spinal vertebrae are urged into the natural elliptical alignment and the joints are lubricated and aligned. An adjustable body strap attachment for encompassing the user's thoracic/lumbo-sacral-pelvic spinal vertebrae region and secured through the frame is attached to an elongate stirrup strap. The stirrup attachment engages slidably on the user's feet/legs for exercising pulling force aligned from the legs and lower body to the spine, thereby imparting decompression force from the lower body to the spine and the lower body muscles including the legs, are stretched and exercised. Additionally a hand held monitor for communicating with a tension gauge for measuring the decompression force exerted by the feet/legs on the lower body and spine may be disposed and integrally attached to the stirrup strap.

Although there has been hereinabove described a specific abdominal muscle and spine-exercising device in accordance with the present invention for the purpose of illustrating the manner in which the invention may be used to advantage, it should be appreciated that the invention is not limited thereto. That is, the present invention may suitably comprise, consist of or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. An exercise device adapted for imparting curvature to a lumbar or sacral spine of a user and for manipulating the spine and intervertebral discs with decompression force, said device comprising:
    a frame comprising a top surface and a bottom surface, the bottom surface configured to rest upon a support surface, wherein the top surface and bottom surface are in a spaced apart relationship forming a hollow portion therebetween;
    at least one inflatable bladder carried by the top surface of the frame, the inflation of the at least one inflatable bladder directly against the user's spine causing said bladder to expand and define an expanded configuration thereby manipulating and redefining the curvature in the spine; and
    a body strap attachment passing through the frame in non-fixed relationship and partially disposed within the hollow portion for encompassing the user's thoracic-sacral spinal region and securing said frame.

2. The device of claim 1, wherein said body strap attachment comprises two ends of a strap configured to adjustably secure the frame against the user's thoracic-lumbarsacral spinal region.

3. The device of claim 1, further comprising a stirrup strap member having a proximal end and a distal end, the proximal end attachable to the body strap attachment thereby connecting to the user's spinal region.

4. The device of claim 3, wherein the proximal end of the stirrup strap member comprises at least one loop configured to fasten the proximal end to the body strap attachment.

5. The device of claim 3, further comprising a stirrup attachable to the stirrup strap member distal end and configured to enable the user's feet or legs to apply decompression force from the lower body to the spine.

6. The device of claim 5, wherein the distal end of the stirrup strap member comprises at least one loop configured to fasten the distal end to the stirrup for enabling pulling forces from the lower body to the spine.

7. The device of claim 5, wherein the stirrup comprises a rigid foot opening configured to enable the user to align the legs or feet with the pelvis and spine.

8. The device of claim 5, wherein the stirrup strap member comprises a tension gauge configured to measure the decompression force exerted by the feet or legs on the lower body, spine, and frame.

9. The device of claim 8, further comprising a handheld monitor in communication with the tension gauge and configured to enable the user to monitor applied decompression or exercise force.

10. The device of claim 1, further comprising at least one wheel rotatably attached to the frame and at least partially extending past the bottom surface of the frame.

11. The device of claim 5, further comprising at least one wheel rotatably attached to the stirrup and at least partially extending past a bottom surface of the stirrup.

12. The device of claim 5, wherein the stirrup comprises a slidably looped band.

13. A method for exercising, comprising the steps of:
    positioning a frame of an exercise device with at least one bladder disposed on a top projection of said frame so that the at least one bladder bears against a spine of a user in order to create traction and/or spinal arc in a lower spinal region and/or to stretch lower body muscle groups and/or leg muscles, the frame comprising a hollow portion between the top projection and a bottom of said frame;
    inflating and exhausting alternatively the at least one bladder to decompress, urge, and/or align the spinal vertebrae; and
    encompassing the user's thoracic-sacral spinal vertebrae region and securing the frame with a body strap attachment, the body strap attachment passing through the frame in non-fixed relationship and partially disposed within the hollow portion.

14. The method of claim 13, further comprising slidably engaging one or more feet or legs of the user into a stirrup of the exercise device, the stirrup coupled to the frame by a stirrup strap member.

15. The method of claim 14, further comprising creating aligned decompression forces between the leg muscles and lower abdominal muscles by pulling the stirruped legs or feet in a direction away from the spine to decompress, urge, and/or align the spinal vertebrae.

16. The method of claim 15, further comprising monitoring the decompression forces between the leg muscles and/or lower abdominal and repeating the pulling of the stirruped legs and/or feet in the direction away from the spine to strengthen the lower body, spine, and legs using a tension gauge.

17. The method of claim 16, wherein the stirrup strap member comprises the tension gauge.

18. The method of claim 13, wherein the exercise device comprises at least one wheel rotatably attached to the frame and at least partially extending past a bottom surface of the frame.

19. The method of claim 14, wherein the exercise device comprises at least one wheel rotatably attached to the stirrup and at least partially extending past a bottom surface of the stirrup.

20. The method of claim 14, further comprising connecting the body strap attachment to the stirrup strap member.

\* \* \* \* \*